United States Patent
Kolb (10) Patent No.: US 6,500,209 B1
(45) Date of Patent: Dec. 31, 2002

(54) INTRAMEDULLARY CENTRALIZER HAVING FINS OF VARYING LENGTH AND ASSOCIATED METHOD OF IMPLANTING AN ORTHOPAEDIC COMPONENT INTO A PATIENT

(75) Inventor: Eric D. Kolb, Ft. Wayne, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/676,354

(22) Filed: Sep. 29, 2000

(51) Int. Cl.7 .................................................. A61F 2/36
(52) U.S. Cl. .................. 623/23.48; 623/23.23
(58) Field of Search ........................... 623/18.11–23.46, 623/23.48; 606/95

(56) References Cited

U.S. PATENT DOCUMENTS

| | | |
|---|---|---|
| 4,012,796 A | 3/1977 | Weisman et al. |
| 4,549,319 A * | 10/1985 | Meyer ........................ 606/100 |
| 4,753,657 A | 6/1988 | Lee et al. |
| 4,770,660 A | 9/1988 | Averill |
| 4,783,192 A | 11/1988 | Wroblewski et al. |
| 5,092,892 A | 3/1992 | Ashby |
| 5,507,831 A | 4/1996 | Burke |
| 5,658,351 A | 8/1997 | Dudasik et al. |
| 5,755,793 A | 5/1998 | Smith et al. |
| 5,984,968 A | 11/1999 | Park |
| 5,997,581 A | 12/1999 | Khalili |

* cited by examiner

Primary Examiner—Corrine McDermott
Assistant Examiner—Thomas Barrett
(74) Attorney, Agent, or Firm—Maginot, Moore & Bowman (57) ABSTRACT

A centralizer for an intramedullary stem of an orthopaedic component that is adapted to be implanted into a medullary canal of a bone includes an annular body having an interior surface and an exterior surface. The centralizer also includes a first exterior fin secured to the exterior surface of the annular body so as to extend outwardly therefrom. The first exterior fin possesses a first length. The centralizer also includes a second exterior fin secured to the exterior surface of the annular body so as to extend outwardly therefrom. The second exterior fin possesses a second length which is greater than the first length. A method of implanting an orthopaedic component into a patient is also disclosed.

11 Claims, 4 Drawing Sheets

Fig. 4 ated method of implanting an orthopaedic component into a patient.

INTRAMEDULLARY CENTRALIZER HAVING FINS OF VARYING LENGTH AND ASSOCIATED METHOD OF IMPLANTING AN ORTHOPAEDIC COMPONENT INTO A PATIENT

TECHNICAL FIELD OF THE INVENTION

The present invention relates generally to a centralizer for a prosthetic component, and more particularly to an intramedullary centralizer having fins of varying length and associated method of implanting an orthopaedic component into a patient.

BACKGROUND OF THE INVENTION

During the lifetime of a patient, it may be necessary to perform a hip replacement procedure on the patient as a result of, for example, disease or trauma. The hip replacement procedure may involve the use of a femoral component which has a head portion that is utilized to replace the natural head portion of the thigh bone or femur. The femoral component typically has an elongated intramedullary stem which is utilized to secure the femoral component to the patient's femur. In particular, the medullary canal of the patient's femur is first surgically prepared (e.g. reamed and/or broached) such that the intramedullary stem of the femoral component may be subsequently implanted therein. Bone cement may then be utilized to secure the femoral component within the medullary canal.

When bone cement is utilized to secure the femoral component within the medullary canal in such a manner, it is desirable to form a relatively even or uniform mantle around the intramedullary stem of the component. Hence, during such implantation of the femoral component into the femur, a mechanical guide or "centralizer" is typically utilized to position the intramedullary stem of the femoral component in a neutral or "centered" position within the medullary canal of the femur. By centering the intramedullary stem within the medullary canal of the femur, the centralizer may advantageously provide for the formation of a relatively uniform bone cement mantle between the intramedullary stem and the surgically prepared interior walls of the medullary canal of the femur.

Centralizers are typically secured to the intramedullary stem of the femoral component prior to implantation thereof. Centralizers have heretofore been classified based on the location along the intramedullary stem at which the centralizer is secured. For example, distal centralizers are secured to the distal end of the stem, whereas mid-shaft centralizers are typically secured to the intramedullary stem at a location between the distal end and the proximal end of the stem. Each type of heretofore designed centralizers have a number of unique drawbacks associated therewith.

For example, a thin mantle may be formed at mid-shaft regions as a result of use of certain heretofore designed distal stabilizers. In particular, even when the distal stabilizer properly centralizes the intramedullary stem at the distal end thereof, an incomplete or slightly thinner bone cement mantle may be formed around the anterior side of the mid-shaft portion of the intramedullary stem. It should be appreciated that an incomplete or thin bone cement mantle may lead to crack propagation in the bone cement or even loosening of the implanted femoral component.

As a result of these and other concerns, a number of mid-shaft centralizers were designed. While heretofore designed mid-shaft stabilizers have been relatively successful at centering the mid-shaft portion of the intramedullary stem (thereby providing a more uniform bone cement mantle around the mid-shaft portion), a number of other problems have been associated with their use. For example, heretofore designed mid-shaft centralizers may have a tendency to tip the stem in the anterior or posterior direction thereby creating a relatively thin (or even incomplete) bone cement mantle at the distal end of the stem.

Another drawback associated with heretofore designed centralizers is the configuration of the interior surfaces of the centralizers. In particular, centralizers which have heretofore been designed often have a smooth interior surface which forms substantially continuous (i.e. line-toline) contact with the outer surface of the stem when the centralizer is secured to the stem. Such centralizers, often referred to as "napkin ring" centralizers, restrict the bone cement from coming into direct contact with the outer surface of the intramedullary stem thereby potentially creating a void or non-bonded region in the cement. The formation of such a void increases the potential of crack propagation.

What is needed therefore is a centralizer which overcomes one or more of the above-mentioned drawbacks. What is particularly needed is a centralizer which centers the intramedullary stem of a femoral component while also facilitating the formation of a relatively uniform bone cement mantle along the entire length of the stem.

SUMMARY OF THE INVENTION

In accordance with one embodiment of the present invention, there is provided a centralizer for an intramedullary stem of an orthopaedic component that is adapted to be implanted into a medullary canal of a bone. The centralizer includes an annular body having an interior surface and an exterior surface. The centralizer also includes a first exterior fin secured to the exterior surface of the annular body so as to extend outwardly therefrom. The first exterior fin possesses a first length. The centralizer also includes a second exterior fin secured to the exterior surface of the annular body so as to extend outwardly therefrom. The second exterior fin possesses a second length which is greater than the first length.

In accordance with another embodiment of the present invention, there is provided a centralizer for an intramedullary stem of a femoral component that is adapted to be implanted into a medullary canal of a femur. The intramedullary stem of the femoral component has a lateral surface, a medial surface, an anterior surface, and a posterior surface. The centralizer includes an annular body having an interior surface and an exterior surface. The interior surface is adapted to receive the intramedullary stem of the femoral component. The centralizer also includes an anterior fin secured to the exterior surface of the annular body so as to extend outwardly from the exterior surface in an anterior direction away from the anterior surface of the intramedullary stem when the centralizer is secured to the femoral component. The anterior fin possesses a first length. The centralizer also includes a lateral fin secured to the exterior surface of the annular body so as to extend outwardly from the exterior surface in a lateral direction away from the lateral surface of the intramedullary stem when the centralizer is secured to the femoral component. The lateral fin possesses a second length. The centralizer further includes a posterior fin secured to the exterior surface of the annular body so as to extend outwardly from the exterior surface in a posterior direction away from the posterior surface of the intramedullary stem when the centralizer is secured to the femoral component. The posterior fin possesses the first length. The centralizer yet further includes a medial fin secured to the exterior surface of the annular body so as to extend outwardly from the exterior surface in a medial direction away from the medial surface of the intramedullary stem when the centralizer is secured to the femoral component. The medial fin possesses the second length. The second length is greater than the first length.

In accordance with a further embodiment of the present invention, there is provided a method of implanting an orthopaedic component into a patient. The method includes the step of securing a centralizer to an intramedullary stem of the orthopaedic component. The centralizer includes an annular body having an interior surface and an exterior surface. The centralizer also includes a first exterior fin secured to the exterior surface of the annular body so as to extend outwardly therefrom. The first exterior fin possesses a first length. The centralizer also includes a second exterior fin secured to the exterior surface of the annular body so as to extend outwardly therefrom. The second exterior fin possessing a second length which is greater than the first length. The method also includes the step of implanting the orthopaedic component into a medullary canal of a bone of the patient.

In accordance with yet another embodiment of the present invention, there is provided a centralizer for an intramedullary stem of an orthopaedic component that is adapted to be implanted into a medullary canal of a bone. The centralizer includes a body having a stem-receiving opening defined therein. The body further has an interior surface and an exterior surface. The centralizer further includes a number of first fins secured to the exterior surface of the body so as to extend outwardly therefrom. The number of first fins each possess a first length. The centralizer further includes a number of second fins secured to the exterior surface of the body so as to extend outwardly therefrom. The number of second fins each possess a second length which is greater than the first length.

It is therefore an object of the present invention to provide a new and useful centralizer for an orthopaedic component.

It is moreover an object of the present invention to provide an improved centralizer for an orthopaedic component.

It is a further object of the present invention to provide a new and useful method of implanting an orthopaedic component into a patient.

It is also an object of the present invention to provide an improved method of implanting an orthopaedic component into a patient.

It is yet another object of the present invention to provide a centralizer which centers the intramedullary stem of a femoral component while also facilitating the formation of a relatively uniform bone cement mantle along the entire length of the stem.

The above and other objects, features, and advantages of the present invention will become apparent from the following description and the attached drawings.

DETAILED DESCRIPTION OF THE INVENTION

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 1:
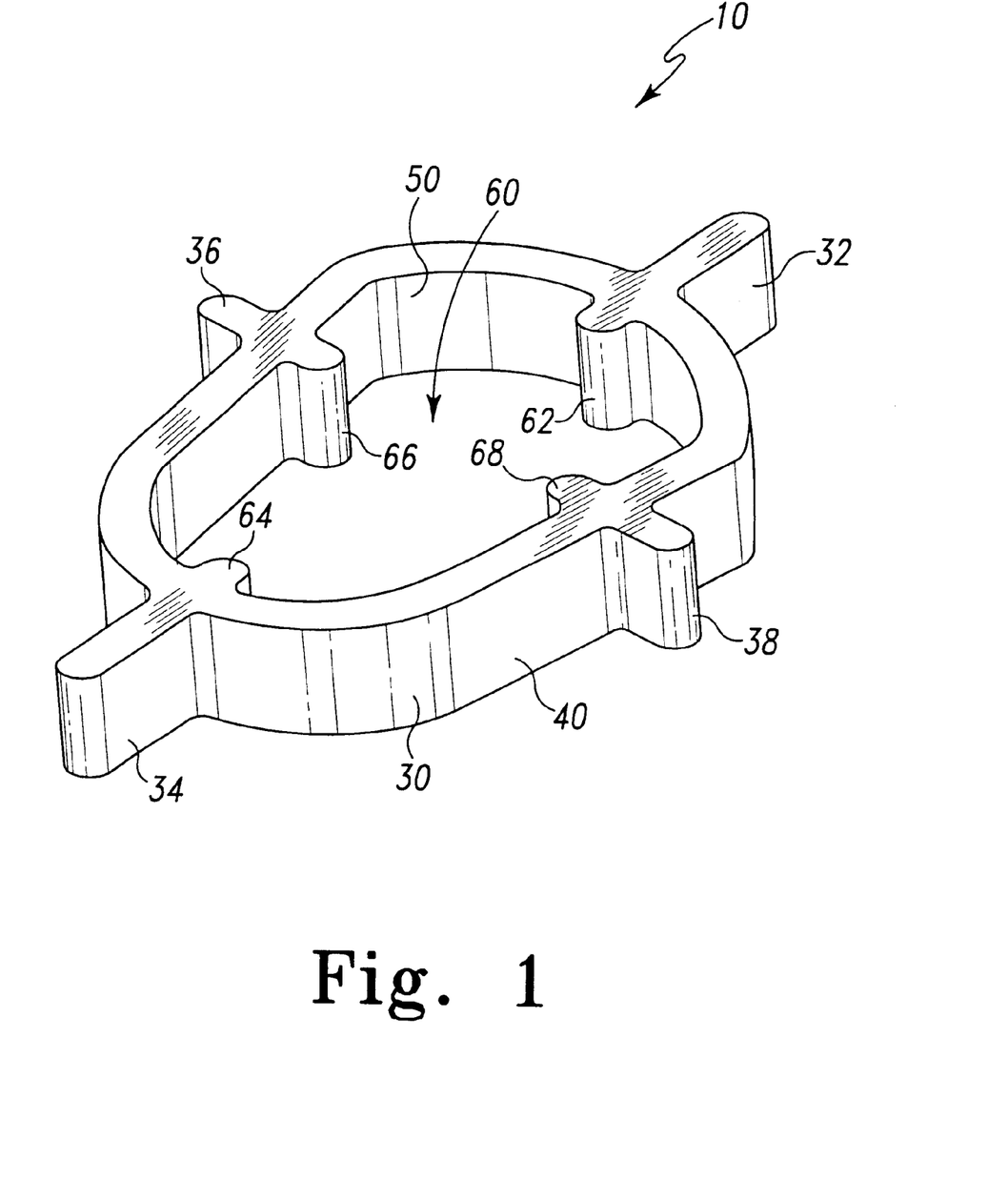
FIG. 1 is a perspective view of a centralizer which incorporates the features of the present invention therein.
Figure 2:
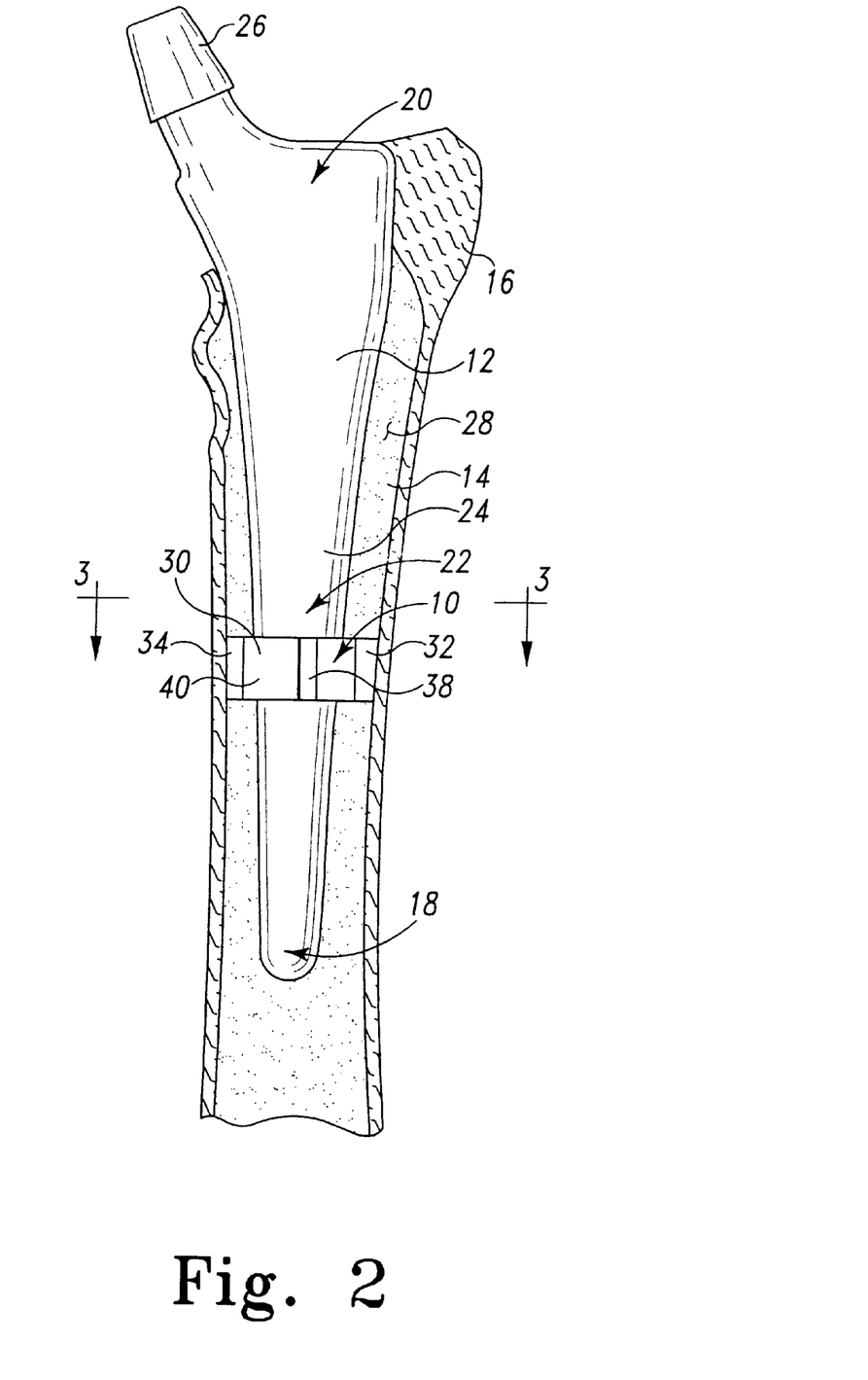
FIG. 2 is a cross sectional view of a femur showing a femoral component and the centralizer of FIG. 1 implanted therein, note that the femoral component and the centralizer are not shown in cross section for clarity of description.
Figure 3:
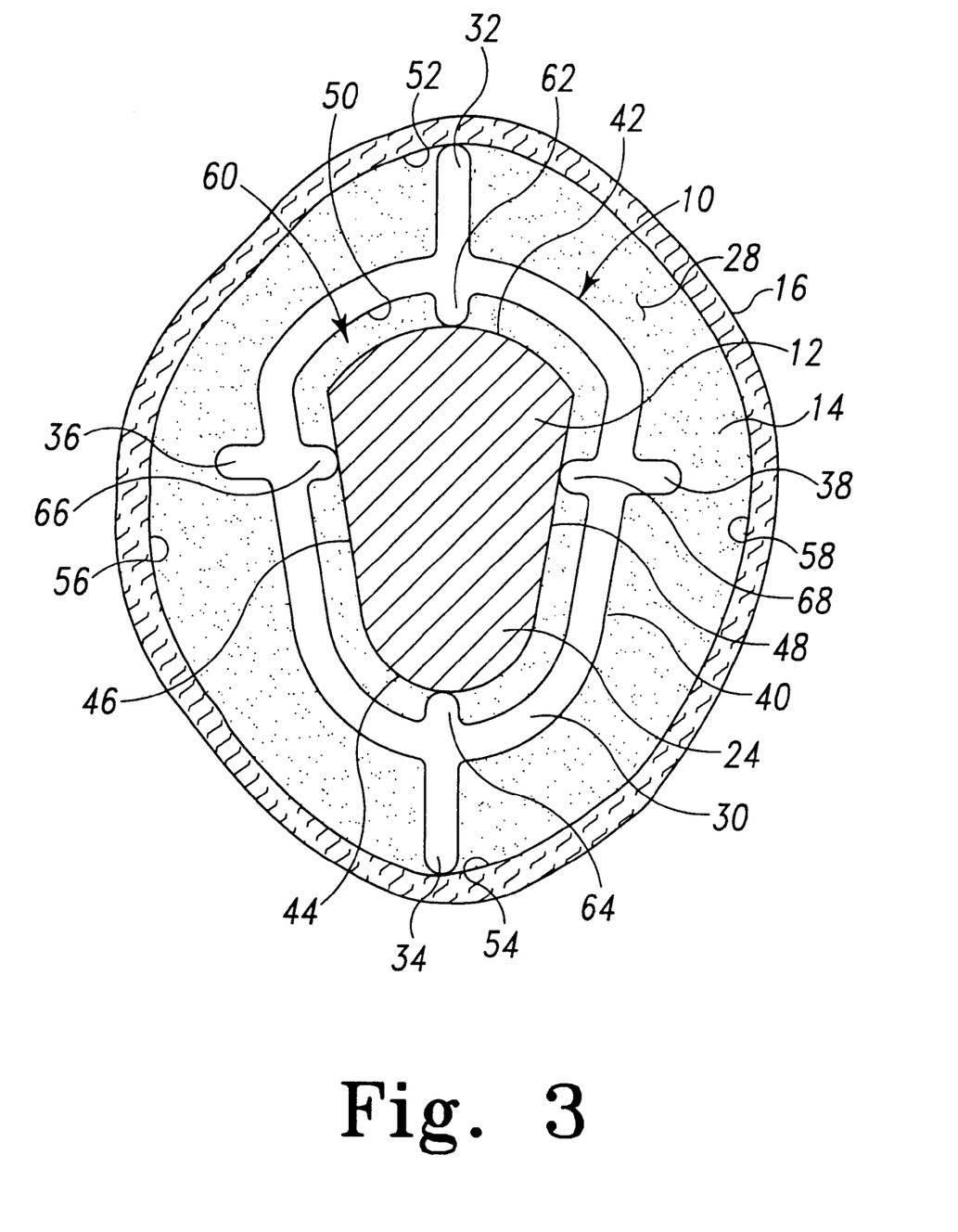
FIG. 3 is a cross sectional view taken along the line 3—3 of FIG. 2, as viewed in the direction of the arrows.

Referring now to FIGS. 1–3, there is shown a centralizer 10 for use during performance of a joint replacement procedure such as a hip replacement procedure. The centralizer 10 is secured to a femoral component 12 prior to implantation of the femoral component 12 into a surgically prepared (e.g. reamed and/or broached) medullary canal 14 of a femur 16. The femoral component 12 includes a trunnion 26 and an intramedullary stem 24 which is implanted or otherwise advanced into the medullary canal 14 of the femur 16. In particular, during performance of a hip replacement procedure, the medullary canal 14 of the femur 16 is prepared (e.g. reamed and/or broached) by the surgeon and thereafter filled with a bone cement 28. Once the medullary canal 14 has been filled with bone cement, the intramedullary stem 24 is advanced into the medullary canal 14 such that the trunnion 26 extends outwardly from the femur 16 as shown in FIG. 2.

As also shown in FIG. 2, the centralizer 10 is preferably embodied as a "mid-shaft" centralizer. In particular, the intramedullary stem 24 of the femoral component 12 has a distal end portion 18 and a proximal end portion 20. A mid-shaft portion 22 of the femoral component 12, as its name implies, is interposed between the distal end portion 18 and the proximal end portion 20. As shown in FIG. 2, the centralizer 10 is secured to the mid-shaft portion 22 of the intramedullary stem 24 when the centralizer 10 is secured to the femoral component 12.

As shown in FIG. 1, the centralizer 10 includes an annular body 30 having an exterior surface 40 and an interior surface 50. The interior surface 50 defines a stem-receiving opening 60 which is adapted to receive the intramedullary stem 24 of the femoral component 12 so as to secure the centralizer 10 to the femoral component 12. It should be appreciated that the annular body 30 of the centralizer 10 may be embodied in any one of a number of different shapes. In particular, the annular body 30 may be embodied in any shape that creates a substantially closed loop or path. For example, the annular body 30 may be somewhat circular in shape (similar to as shown in FIG. 1), or may alternatively be embodied substantially non-circular in shape.

The interior surface 50 of the centralizer body 30 also has a number of interior fins secured thereto which extend inwardly into the stem-receiving opening 60. As shall be discussed below in greater detail, the interior fins provide numerous advantages to the centralizer 10 of the present invention. The exterior surface 40, on the other hand, has a number of exterior fins secured thereto which extend outwardly therefrom. In particular, the centralizer 10 includes a lateral exterior fin 32, a medial exterior fin 34, and anterior exterior fin 36, and a posterior exterior fin 38. As can be seen from FIGS. 1 and 3, the lateral fin 32 and the medial fin 34 are secured to substantially opposite sides of the centralizer body 30 from one another, whereas the anterior fin 36 and the posterior fin 38 are secured to substantially opposite sides of the body 30 from one another. In particular, the names associated with each of the exterior fins 32, 34, 36, 38 refer to the direction in which they are arranged when the centralizer 10 is secured to the intramedullary stem 24 of the femoral component 12. Hence, as shown in FIG. 3, when secured to the intramedullary stem 24 and implanted into the femur 16, the lateral fin 32 extends away from a lateral surface 42 of the intramedullary stem 24 in a lateral direction toward a lateral surface 52 of the medullary canal 14. Similarly, the medial fin 34 extends away from a medial surface 44 of the intramedullary stem 24 in a medial direction toward a medial surface 54 of the medullary canal 14, whereas the anterior fin 36 extends away from an anterior surface 46 of the intramedullary stem 24 in an anterior direction toward an anterior surface 56 of the medullary canal 14. In a similar manner, the posterior fin 38 extends away from a posterior surface 48 of the intramedullary stem 24 in a posterior direction toward a posterior surface 58 of the medullary canal 14.

Moreover, the exterior fins 32, 34, 36, 38 are configured in various lengths. Specifically, one or more of the fins is configured to be greater in length (i.e. longer) than the remaining fins. In one exemplary embodiment, both the lateral fin 32 and the medial fin 34 possess a length which is greater than the length of either the anterior fin 36 or the posterior fin 38. In a more specific exemplary embodiment, both the lateral fin 32 and the medial fin 34 extend outwardly from the exterior surface 40 of the body 30 by a distance of three millimeters (3 mm), whereas both the anterior fin 36 and the posterior fin 38 extend outwardly from the exterior surface 40 of the centralizer body 30 by a distance of one to two millimeters (1–2 mm).

Even though any of the fins 32, 34, 36, 38 may be configured longer than the remaining fins, it is preferable that the lateral fin 32 and the medial fin 34 be configured to be longer than the anterior fin 36 and the posterior fin 38. In particular, as shown in FIG. 3, it is preferable to configure both the lateral fin 32 and the medial fin 34 long enough to contact the surgically prepared (e.g. reamed and/or broached) surfaces of the medullary canal 14. Conversely, it is preferable to configure both the anterior fin 36 and the posterior fin 38 short enough to be spaced apart from the surgically prepared surfaces of the medullary canal 14 in order not to contact the same. Such a configuration provides a number of advantages to the centralizer 10 of the present invention. For example, use of longer lateral and medial fins 32, 34 provides for a relatively uniform, thick bone cement mantle around the mid-shaft portion 22 of the intramedullary stem 24 thereby overcoming the problems associated with insufficient cement mantles created by certain heretofore designed distal tip centralizers.

However, unlike certain heretofore designed mid-shaft centralizers, the configuration of the centralizer 10 of the present invention does not tip or otherwise force the distal end portion 18 of the intramedullary stem 24 into contact with the wall surfaces of the medullary canal 14 of the femur 16. In particular, the anterior and posterior fins 36, 38 are configured to be long enough to prevent a deficiency in the bone cement mantle from being formed in the anterior direction surrounding the mid-shaft portion 22 of the intramedullary stem 24, but small enough so as not to "push" the distal end portion 18 of the stem 24 into contact with the posterior surface 58 of the medullary canal 12. In other words, in the specific embodiment shown in FIGS. 1–3, the anterior and posterior fins 36, 38 are configured to be short enough so as to be spaced apart from or otherwise not contact the surgically prepared surfaces of the medullary canal 12 (i.e. the anterior surface 56 and the posterior surface 58, respectively) when the centralizer 10 itself is centered or otherwise positioned in the center of the medullary canal 12 (as shown in FIG. 3). However, the length of the anterior and posterior fins 36, 38 is configured to be long enough to maintain a desirable thickness in the bone cement mantle in the event that movement of the intramedullary stem 24 by the surgeon causes one or both of the anterior or posterior fins 36, 38 to actually contact the prepared surfaces of the medullary canal 12. Hence, the configuration of the anterior and posterior fins 36, 38 grants the surgeon the freedom to move the stem 24 in the anterior/posterior directions in order to centralize the distal end portion 18 of the stem 24 while also maintaining a desirable tickness in the bone cement mantle surrounding the mid-shaft portion 22 of the stem 24.

Figure 4:
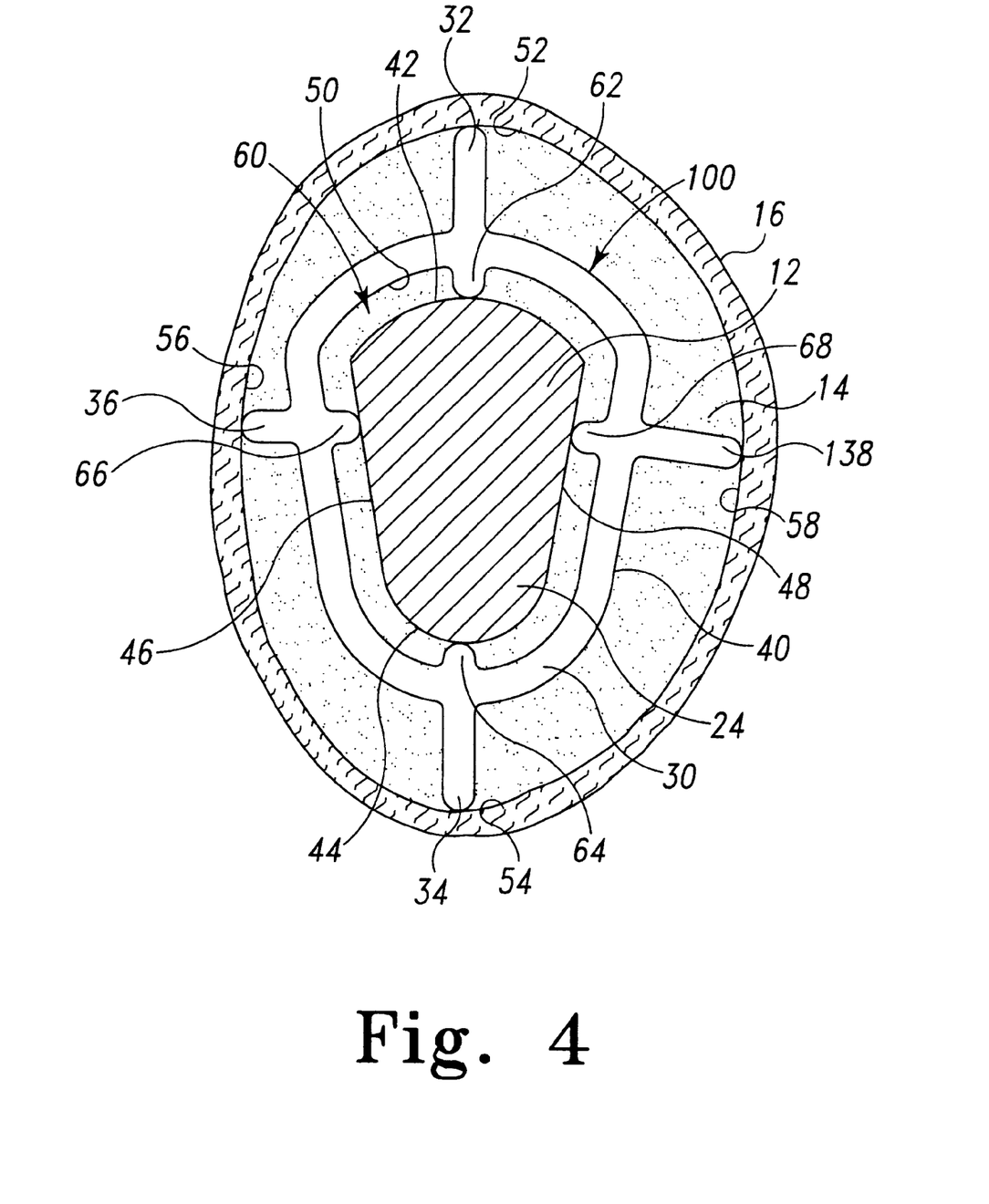
FIG. 4 is a view similar to FIG. 3, but showing a second embodiment of a centralizer which incorporates the features of the present invention therein.

Hence, as described herein, it should be appreciated that the length of any of the fins 32, 34, 36, 38 may be varied relative to the remaining fins 32, 34, 36, 38. In particular, although specific fin configurations are shown in FIGS. 3 and 4, it should be appreciated that any fin configuration which utilizes one or more fins of varying lengths may be utilized to achieve certain of the advantages of the centralizer design of the present invention. For example, a centralizer may be constructed which utilizes one relatively long exterior fin along with one or more relatively short fins.

Moreover, it should also be appreciated that although the centralizer 10 of the present invention is herein described as having four exterior fins (i.e. the fins 32, 34, 36, 38), and has significant advantages thereby in the present invention, certain of such advantages may be achieved by use of a different number of fins. In particular, the centralizer of the present invention may be configured to include less than four fins or greater than four fins and still achieve certain of the advantages associated with the concepts of the present invention.

As shown in FIGS. 1 and 3, the centralizer 10 also includes a lateral interior fin 62, a medial interior fin 64, and anterior interior fin 66, and a posterior interior fin 68. As with the exterior fins, the names associated with each of the interior fins 62, 64, 66, 68 refer to the direction in which they are arranged when the centralizer 10 is secured to the intramedullary stem 24 of the femoral component 12. In particular, as shown in FIG. 3, when the centralizer 10 is secured to the intramedullary stem 24, the lateral fin 62 extends toward the lateral surface 42 of the intramedullary stem 24, whereas the medial fin 64 extends toward the medial surface 44 of the intramedullary stem 24. Similarly, the anterior fin 66 extends toward the anterior surface 46 of the intramedullary stem 24, whereas the posterior fin 68 extends toward the posterior surface 48 of the intramedullary stem 24.

As shown in FIG. 3, the tips of each of the interior fins 62, 64, 66, 68 contact the respective outer surfaces 42, 44, 46, 48 of the intramedullary stem 24. As a result of such contact, the interior surface 50 of the centralizer body 30 is spaced apart from the outer surfaces 42, 44, 46, 48 of the intramedullary stem 24. Such an arrangement provides a number of advantages to the centralizer 10. For example, such an arrangement provides point-to-point contact between the centralizer 10 and the respective outer surfaces 42, 44, 46, 48 of the intramedullary stem 24 (as opposed to the line-to-line contact created by the use of heretofore designed "napkin ring" style centralizers). Such point-to-point contact is desirable since it allows the bone cement 28 to "flow" between the centralizer 10 and the intramedullary stem 24 during implantation of the stem into the medullary canal 14 of the femur 16. This provides for enhanced surface contact area at the interface between the bone cement 28 and the intramedullary stem 24 thereby overcoming the above-described drawbacks associated with napkin ring style centralizers.

As shown in FIG. 3, each of the interior fins 62, 64, 66, 68 is configured to possess a substantially equal length. Moreover, in one exemplary embodiment, each of the interior fins 62, 64, 66, 68 is configured to possess a length which is less (i.e. shorter) than the length of each of the exterior fins 32, 34, 36, 38. However, it should be appreciated that the length of any of the individual interior fins 62, 64, 66, 68 may be altered into a configuration (including varying lengths relative to one another) that fits the needs of a given design of the centralizer 10.

As described above, each of the exterior fins 32, 34, 36, 38 and the interior fins 62, 64, 66, 68 are secured to the centralizer body 30. In one exemplary embodiment, each of the exterior fins and the interior fins are integrally formed with the centralizer body 30. In a more specific exemplary embodiment, the centralizer body 30, along with each of the exterior fins and the interior fins, are integrally molded with one another and are constructed from an acrylic polymeric material such as polymethyl methacrylate (PMMA). The use of PMMA provides the centralizer 10 with a number of advantages. For example, PMMA, in a powder form, is commonly utilized as a component of bone cement. Indeed, PMMA powder is generally premixed with a liquid acrylic monomer system, which generally includes methyl methacrylate (MMA), so as to produce a substance which functions as bone cement. Hence, construction of the centralizer 10 from PMMA provides for enhanced "integration" of the centralizer 10 into the bone cement 28 thereby reducing the possibility for crack formation and/or propagation near the interface of the centralizer 10 and the bone cement 28.

OPERATION OF THE PRESENT INVENTION

In operation, the centralizer 10 of the present invention is utilized in the performance of a hip replacement procedure in order to center the femoral component during implantation of the femoral component into the medullary canal of the femur. In order to do so, the medullary canal 14 of the femur 16 is first reamed, broached, or otherwise surgically prepared by the surgeon. Thereafter, the medullary canal 14 of the femur 16 is filled with bone cement 28. Once the medullary canal 14 has been filled with bone cement 28, the femoral component 12 may then be implanted into the femur 16.

However, prior to implantation, the centralizer 10 is first secured to the intramedullary stem 24 of the femoral component 12. In order to do so, the intramedullary stem 24 of the femoral component 12 is advanced through the stem-receiving opening 60 of the centralizer body 30. In particular, the surgeon aligns the centralizer 10 with the intramedullary stem 24 so that (1) the lateral interior fin 62 is aligned with the lateral outer surface 42 of the stem 24, (2) the medial interior fin 64 is aligned with the medial outer surface 44 of the stem, (3) the anterior interior fin 66 is aligned with the anterior outer surface 46 of the stem 24, and (4) the posterior interior fin 68 is aligned with the posterior outer surface 48 of the stem 24. Thereafter, the surgeon advances the centralizer 10 and the femoral component 12 relative one another so as to cause the distal end portion 18 of the stem 24 to be advanced through the stem-receiving opening 60 of the centralizer body 30.

The surgeon then advances the centralizer 10 upwardly along the intramedullary stem 24 onto the mid-shaft portion 22 of the stem 24 until the tips of the interior fins 62, 64, 66, 68 are advanced into contact with the tapered outer surface of the stem 24. As described above, when the centralizer 10 is secured to the intramedullary stem 24 and implanted into the femur 16, the lateral fin 32 extends away from the lateral surface 42 of the intramedullary stem 24, whereas the medial fin 34 extends away from the medial surface 44 of the intramedullary stem 24. In a similar manner, the anterior fin 36 extends away from the anterior surface 46 of the intramedullary stem 24, whereas the posterior fin 38 extends away from the posterior surface 48 of the intramedullary stem 24.

Once the centralizer 10 is secured to the femoral component 12 in such a manner, the femoral component 12 is implanted into the femur 16. In particular, the distal end portion 18 of the stem 24 is advanced through the surgically prepared opening in the femur 16 and into the medullary canal 14. The femoral component 12 continues to be advanced into the medullary canal 14 until it is fully seated, as shown in FIGS. 2 and 3. When fully seated, the exterior lateral fin 32 and medial fin 34 contact the surgically prepared inner surfaces 52, 54, respectively, of the medullary canal 14. Moreover, the anterior fin 36 and the posterior fin 38 are spaced apart from the surgically prepared inner surfaces 56, 58, respectively, of the medullary canal 14 so as to allow the surgeon to move the proximal end portion and the distal end portion 18 of the stem 12 into their respective centered or "neutral" positions thereby completing the implantation process.

Hence, as described herein, the centralizer 10 of the present invention provides numerous advantages over heretofore designed centralizers. For example, the centralizer 10 of the present invention provides for a relatively uniform, thick bone cement mantle around the mid-shaft portion 22 of the intramedullary stem 24 thereby overcoming the problems associated with insufficient mid-shaft cement mantles caused by certain heretofore designed distal tip centralizers. However, unlike a number of heretofore designed mid-shaft centralizers, the configuration of the centralizer 10 of the present invention does not tip or otherwise force the distal end portion 18 of the intramedullary stem 24 into contact with the wall surfaces of the medullary canal 14 of the femur 16.

Moreover, the centralizer 10 of the present invention allows the bone cement 28 to "flow" between the centralizer 10 and the intramedullary stem 24 during implantation of the stem 24 into the medullary canal 14 of the femur 16 in order to provide enhanced contact surface area at the interface between the bone cement 28 and the intramedullary stem 24 thereby overcoming the above-described drawbacks associated with napkin ring style centralizers.

While the invention has been illustrated and described in detail in the drawings and foregoing description, such an illustration and description is to be considered as exemplary and not restrictive in character, it being understood that only the preferred embodiments have been shown and described and that all changes and modifications that come within the spirit of the invention are desired to be protected.

There are a plurality of advantages of the present invention arising from the various features of the centralizer and associated method described herein. It will be noted that alternative embodiments of the centralizer and associated method of the present invention may not include all of the features described yet still benefit from at least some of the advantages of such features. Those of ordinary skill in the art may readily devise their own implementations of a centralizer and associated method that incorporate one or more of the features of the present invention and fall within the spirit and scope of the present invention as defined by the appended claims.

For example, it should be appreciated that certain of the advantages associated with the centering of the femoral component 12 in its desired location within the femur 16 may be achieved by use of a centralizer without the interior fins 62, 64, 66, 68. More specifically, although the centralizer 10 is described herein as being configured to include the interior fins 62, 64, 66, 68, and has significant advantages thereby, certain of such advantages may be achieved by configuring the centralizer as a "napkin ring" centralizer which has exterior fins of varying lengths as described above.

Moreover, although the centralizer 10 has herein been described as a femoral component centralizer, it should be appreciated that the concepts described herein may be utilized in conjunction with other types of orthopaedic components. For example, the concepts of the present invention may be utilized in the construction of a centralizer that is to be utilized to center a humeral component during performance of a shoulder replacement procedure.

Yet further, as shown in FIG. 4, there is shown another embodiment of a centralizer (hereinafter referred to with reference numeral 100) which incorporates the features of the present invention therein. The centralizer 100 is somewhat similar to the centralizer 10. Accordingly, the centralizer 100 includes a number of features which are identical to certain of the features previously discussed in regard to the centralizer 10. The same reference numerals are utilized in FIG. 4 to designate identical features which were previously discussed in regard to FIGS. 1–3 and additional discussion thereof is not warranted.

The centralizer 100 is essentially the same as the centralizer 10 except that the posterior fin 38 of the centralizer 10 has been replaced with a posterior fin 138. The posterior fin 138 is not the same length as the anterior fin 36, but rather is configured to be longer than the anterior fin 36. Moreover, as can be seen in FIG. 4, the length of each of the exterior fins 32, 34, 36, 138 has been altered so that the tips of each of the fins 32, 34, 36, 138 contact their respective surgically prepared surfaces 52, 54, 56, 58 of the medullary canal 14. The configuration of the centralizer 100 may be desirable since, in certain cases, it may provide enhanced (e.g. more consistent) centralization of the femoral component 12 within the femur 16.

What is claimed is:

1. A centralizer for an intramedullary stem of an orthopaedic component that is adapted to be implanted into a medullary canal of a bone, said centralizer comprising:

an annular body having an interior surface and an exterior surface;

a first exterior fin secured to said exterior surface of said annular body, said first exterior fin extending outwardly away from said exterior surface for a first distance;

a second exterior fin secured to said exterior surface of said annular body, said second exterior fin extending outwardly away from said exterior surface for a second distance which is greater than said first distance;

a third exterior fin secured to said exterior surface of said annular body, said third exterior fin extending outwardly away from said exterior surface for said first distance; and a fourth exterior fin secured to said exterior surface of said annular body, said fourth exterior fin extending outwardly away from said exterior surface for said second distance, wherein said intramedullary stem of said orthopaedic component has a lateral surface, a medial surface, an anterior surface, and a posterior surface, wherein said first exterior fin extends outwardly in an anterior direction away from said anterior surface of said intramedullary stem when said centralizer is secured to said orthopaedic component, wherein said second exterior fin extends outwardly in a lateral direction away from said lateral surface of said intramedullary stem when said centralizer is secured to said orthopaedic component, wherein said third exterior fin extends outwardly in a posterior direction away from said posterior surface of said intramedullary stem when said centralizer is secured to said orthopaedic component, and wherein said fourth exterior fin extends outwardly in a medial direction away from said medial surface of said intramedullary stem when said centralizer is secured to said orthopaedic component.

2. A centralizer for an intramedullary stem of an orthopaedic component that is adapted to be implanted into a medullary canal of a bone, said centralizer comprising:

an annular body having an interior surface and an exterior surface;

a first exterior fin secured to said exterior surface of said annular body, said first exterior fin extending outwardly away from said exterior surface for a first distance;

a second exterior fin secured to said exterior surface of said annular body, said second exterior fin extending outwardly away from said exterior surface for a second distance which is greater than said first distance;

a third exterior fin secured to said exterior surface of said annular body, said third exterior fin extending outwardly away from said exterior surface for said first distance; and a fourth exterior fin secured to said exterior surface of said annular body, said fourth exterior fin extending outwardly away from said exterior surface for said second distance, wherein said medullary canal of said bone is defined by a lateral surface, a medial surface, an anterior surface, and a posterior surface, wherein said first exterior fin extends outwardly in an anterior direction toward said anterior surface of medullary canal when (i) said centralizer is secured to said orthopaedic component, and (ii) said orthopaedic component is implanted into said medullary canal of said bone, wherein said second exterior fin extends outwardly in a lateral direction toward said lateral surface of medullary canal when (i) said centralizer is secured to said orthopaedic component, and (ii) said orthopaedic component is implanted into said medullary canal of said bone, wherein said third exterior fin extends outwardly in a posterior direction toward said posterior surface of medullary canal when (i) said centralizer is secured to said orthopaedic component, and (ii) said orthopaedic component is implanted into said medullary canal of said bone, and wherein said fourth exterior fin extends outwardly in a medial direction toward said medial surface of medullary canal when (i) said centralizer is secured to said orthopaedic component, and (ii) said orthopaedic component is implanted into said medullary canal of said bone.

3. A centralizer for an intramedullary stem of an orthopaedic component that is adapted to be implanted into a medullary canal of a bone, said centralizer comprising:

an annular body having an interior surface and an exterior surface;

a first exterior fin secured to said exterior surface of said annular body, said first exterior fin extending outwardly away from said exterior surface for a first distance; and a second exterior fin secured to said exterior surface of said annular body, said second exterior fin extending outwardly away from said exterior surface for a second distance which is greater than said first distance, wherein said intramedullary stem of said orthopaedic component has a distal end portion and a proximal end portion with a mid-shaft portion interposed therebetween, and wherein said centralizer is positioned on said mid-shaft portion of said intramedullary stem when said centralizer is secured to said orthopaedic component.

4. A centralizer for an intramedullary stem of a femoral component that is adapted to be implanted into a medullary canal of a femur, said intramedullary stem of said femoral component having a lateral surface, a medial surface, an anterior surface, and a posterior surface, said centralizer comprising:

an annular body having an interior surface and an exterior surface, said interior surface being adapted to receive said intramedullary stem of said femoral component;

an anterior fin secured to said exterior surface of said annular body so as to extend outwardly from said exterior surface in an anterior direction away from said anterior surface of said intramedullary stem when said centralizer is secured to said femoral component, said anterior fin possessing a first length;

a lateral fin secured to said exterior surface of said annular body so as to extend outwardly from said exterior surface in a lateral direction away from said lateral surface of said intramedullary stem when said centralizer is secured to said femoral component, said lateral fin possessing a second length;

a posterior fin secured to said exterior surface of said annular body so as to extend outwardly from said exterior surface in a posterior direction away from said posterior surface of said intramedullary stem when said centralizer is secured to said femoral component, said posterior fin possessing said first length; and a medial fin secured to said exterior surface of said annular body so as to extend outwardly from said exterior surface in a medial direction away from said medial surface of said intramedullary stem when said centralizer is secured to said femoral component, said medial fin possessing said second length, wherein said second length is greater than said first length.

5. The centralizer of claim 4, wherein each of said first exterior fin, said second exterior fin, said third exterior fin, and said fourth exterior fin is integrally formed with said annular body.

6. The centralizer of claim 4, further comprising a number of interior fins secured to said interior surface of said annular body so as to extend therefrom, wherein:

each of said number of interior fins includes a fin tip, and said fin tip of each of said number of interior fins contacts an outer surface of said intramedullary stem of said femoral component so as to space said interior surface of said annular body apart from said outer surface of said intramedullary stem when said centralizer is secured to said femoral component.

7. The centralizer of claim 6, wherein each of said number of interior fins possesses a third length which is less than both said first length and said second length.

8. The centralizer of claim 4, wherein:

both said lateral fin and said medial fin contact a surgically prepared surface of said medullary canal of said femur when (i) said centralizer is secured to said femoral component, and (ii) said femoral component is implanted into said medullary canal of said femur, and both said anterior fin and said posterior fin are spaced apart from said surgically prepared surface of said medullary canal of said femur when (i) said centralizer is secured to said femoral component, and (ii) said femoral component is implanted into said medullary canal of said femur.

9. A method of implanting an orthopaedic component into a patient, comprising the steps of:

securing a centralizer to an intramedullary stem of said orthopaedic component, said centralizer comprising (i) an annular body having an interior surface and an exterior surface, (ii) a first exterior fin secured to said exterior surface of said annular body, said first exterior fin extending outwardly away from said exterior surface for a first distance, and (iii) a second exterior fin secured to said exterior surface of said annular body, said second exterior fin extending outwardly away from said exterior surface for a second distance which is greater than said first distance; and implanting said orthopaedic component into a medullary canal of a bone of said patient, wherein said centralizer further comprises (i) a third exterior fin secured to said exterior surface of said annular body, said third exterior fin extending outwardly away from said exterior surface for said first distance, and (ii) a fourth exterior fin secured to said exterior surface of said annular body, said fourth exterior fin extending outwardly away from said exterior surface for said second distance, wherein said intramedullary stem of said orthopaedic component has a lateral surface, a medial surface, an anterior surface, and a posterior surface, and wherein said securing step further includes the step of securing said centralizer to said intramedullary stem of said orthopaedic component such that (i) said first exterior fin extends outwardly in an anterior direction away from said anterior surface of said intramedullary stem, (ii) said second exterior fin extends outwardly in a lateral direction away from said lateral surface of said intramedullary stem, (iii) said third exterior fin extends outwardly in a posterior direction away from said posterior surface of said intramedullary stem, and (iv) said fourth exterior fin extends outwardly in a medial direction away from said medial surface of said intramedullary stem.

10. A method of implanting an orthopaedic component into a patient, comprising the steps of:

securing a centralizer to an intramedullary stem of said orthopaedic component, said centralizer comprising (i) an annular body having an interior surface and an exterior surface, (ii) a first exterior fin secured to said exterior surface of said annular body, said first exterior fin extending outwardly away from said exterior surface for a first distance, and (iii) a second exterior fin secured to said exterior surface of said annular body, said second exterior fin extending outwardly away from said exterior surface for a second distance which is greater than said first distance; and implanting said orthopaedic component into a medullary canal of a bone of said patient, wherein said centralizer further comprises (i) a third exterior fin secured to said exterior surface of said annular body, said third exterior fin extending outwardly away from said exterior surface for said first distance, and (ii) a fourth exterior fin secured to said exterior surface of said annular body, said fourth exterior fin extending outwardly away from said exterior surface for said second distance, wherein said medullary canal of said bone is defined by a lateral surface, a medial surface, an anterior surface, and a posterior surface, and wherein said implanting step further includes the step of implanting said orthopaedic component into said medullary canal of said bone such that (i) said first exterior fin extends outwardly in an anterior direction toward said anterior surface of medullary canal, (ii) said second exterior fin extends outwardly in a lateral direction toward said lateral surface of medullary canal, (iii) said third exterior fin extends outwardly in a posterior direction toward said posterior surface of medullary canal, and (iv) said fourth exterior fin extends outwardly in a medial direction toward said medial surface of medullary canal.

11. A centralizer for an intramedullary stem of an orthopaedic component that is adapted to be implanted into a medullary canal of a bone, said centralizer comprising:

a body having a stem-receiving opening defined therein, said body further having an interior surface and an exterior surface;

a number of first fins secured to said exterior surface of said body, said number of first fins each extending outwardly away from said exterior surface for a first distance; and a number of second fins secured to said exterior surface of said body, said number of second fins each extending outwardly away from said exterior surface for a second distance which is greater than said first distance, wherein said number of first fins consists of one fin, and wherein said number of second fins consists of three fins.

* * * * *